United States Patent
Myllykangas et al.

(10) Patent No.: US 12,193,822 B2
(45) Date of Patent: Jan. 14, 2025

(54) PHYSIOLOGICAL MEASUREMENT SYSTEM, BIO-SIGNAL PROCESSING UNIT AND METHOD

(71) Applicant: BITTIUM BIOSIGNALS OY, Kuopio (FI)

(72) Inventors: Juha Myllykangas, Kuopio (FI); Sami Hynynen, Kuopio (FI)

(73) Assignee: Bittium Biosignals Oy, Kuopio (FI)

( * ) Notice: Subject to any disclaimer, the term of this patent is extended or adjusted under 35 U.S.C. 154(b) by 1081 days.

(21) Appl. No.: 17/106,732

(22) Filed: Nov. 30, 2020

(65) Prior Publication Data
US 2022/0167898 A1    Jun. 2, 2022

(51) Int. Cl.
A61B 5/273   (2021.01)
A61B 5/00    (2006.01)
A61B 5/28    (2021.01)
A61B 5/308   (2021.01)

(52) U.S. Cl.
CPC .............. *A61B 5/28* (2021.01); *A61B 5/002* (2013.01); *A61B 5/273* (2021.01); *A61B 5/308* (2021.01); *A61B 2562/227* (2013.01)

(58) Field of Classification Search
CPC .......... A61B 5/28; A61B 5/273; A61B 5/308; A61B 5/002; A61B 2562/227
See application file for complete search history.

(56) References Cited

U.S. PATENT DOCUMENTS

| | | | |
|---|---|---|---|
| 2012/0094260 A1* | 4/2012 | Akins ................. | A61B 5/6824 434/219 |
| 2012/0095315 A1* | 4/2012 | Tenbarge ............. | G16H 40/63 600/365 |

(Continued)

FOREIGN PATENT DOCUMENTS

WO    2015/113322    8/2015

OTHER PUBLICATIONS

Extended European Search Report issued on Aug. 30, 2022 in corresponding European Application No. 21210703.1, 3 pages.

*Primary Examiner* — Adam Z Minchella
(74) *Attorney, Agent, or Firm* — Nixon & Vanderhye PC

(57) ABSTRACT

A physiological measurement system comprises a digital module, which receives an analog bio-signal, a digital unit, which converts the at least one analog bio-signal into a digital signal form, and a first 5-pin-USB-connector, which output the bio-signal in the digital signal form. A bio-signal processing unit, which comprises a counter 5-pin-USB-connector, which is connected with the first 5-pin-USB-connector and receives the bio-signal from the digital module, and alternatively receives analog bio-signal in an analog signal form. The bio-signal processing unit distinguishes between the digital and analog signals and performs: an electric connection of the counter 5-pin-USB-connector with an input of an analog-to-digital converter circuit, an output of which is electrically connected with a digital data processing unit of the bio-signal processing unit, in response to detection of the analog signal received from the counter 5-pin-USB-connector, and an electric connection of the counter 5-pin-USB-connector with the digital data processing unit in response to detection of the digital signal received from the counter 5-pin-USB connector.

20 Claims, 3 Drawing Sheets

(56) References Cited

U.S. PATENT DOCUMENTS

| | | | | |
|---|---|---|---|---|
| 2012/0200173 A1* | 8/2012 | Liu | ................... | G06F 1/266 |
| | | | | 307/130 |
| 2012/0215277 A1* | 8/2012 | Berg | ................ | A61B 5/308 |
| | | | | 607/32 |
| 2012/0306662 A1* | 12/2012 | Vosch | ................. | H04Q 9/00 |
| | | | | 340/870.07 |
| 2017/0281013 A1* | 10/2017 | Natarajan | ........... | A61B 5/002 |
| 2019/0334304 A1* | 10/2019 | Myllykangas | ...... | H01R 33/97 |
| 2020/0305749 A1 | 10/2020 | Myllykangas | | |

\* cited by examiner

PHYSIOLOGICAL MEASUREMENT SYSTEM, BIO-SIGNAL PROCESSING UNIT AND METHOD

FIELD

The invention relates to a physiological measurement system, a bio-signal processing unit and a physiological measurement method.

BACKGROUND

The amount of connector pins of a standard 5-pin-USB-connector restrict possible analog accessories and measurement interfaces that can be connected to bio-signal measurement devices.

A typical solution is to change the USB 2.0 standard connector to something else like USB 3.1 type C, for example, to gain more pins on the connectors. However, such a replacement has significant drawbacks. The connector is more complex, which results in more expensive, larger, non-standard and/or have significantly smaller contact pitch that create a risk for short-circuiting etc. All these things combined with a typical IP67-requirement make the connector selection difficult.

Hence, an improvement would be welcome.

BRIEF DESCRIPTION

The present invention seeks to provide an improvement in the measurements.

The invention is defined by the independent claims. Embodiments are defined in the dependent claims.

LIST OF DRAWINGS

Example embodiments of the present invention are described below, by way of example only, with reference to the accompanying drawings, in which FIG. 1 illustrates an example of a physiological measurement system;

DESCRIPTION OF EMBODIMENTS

Figure 1:
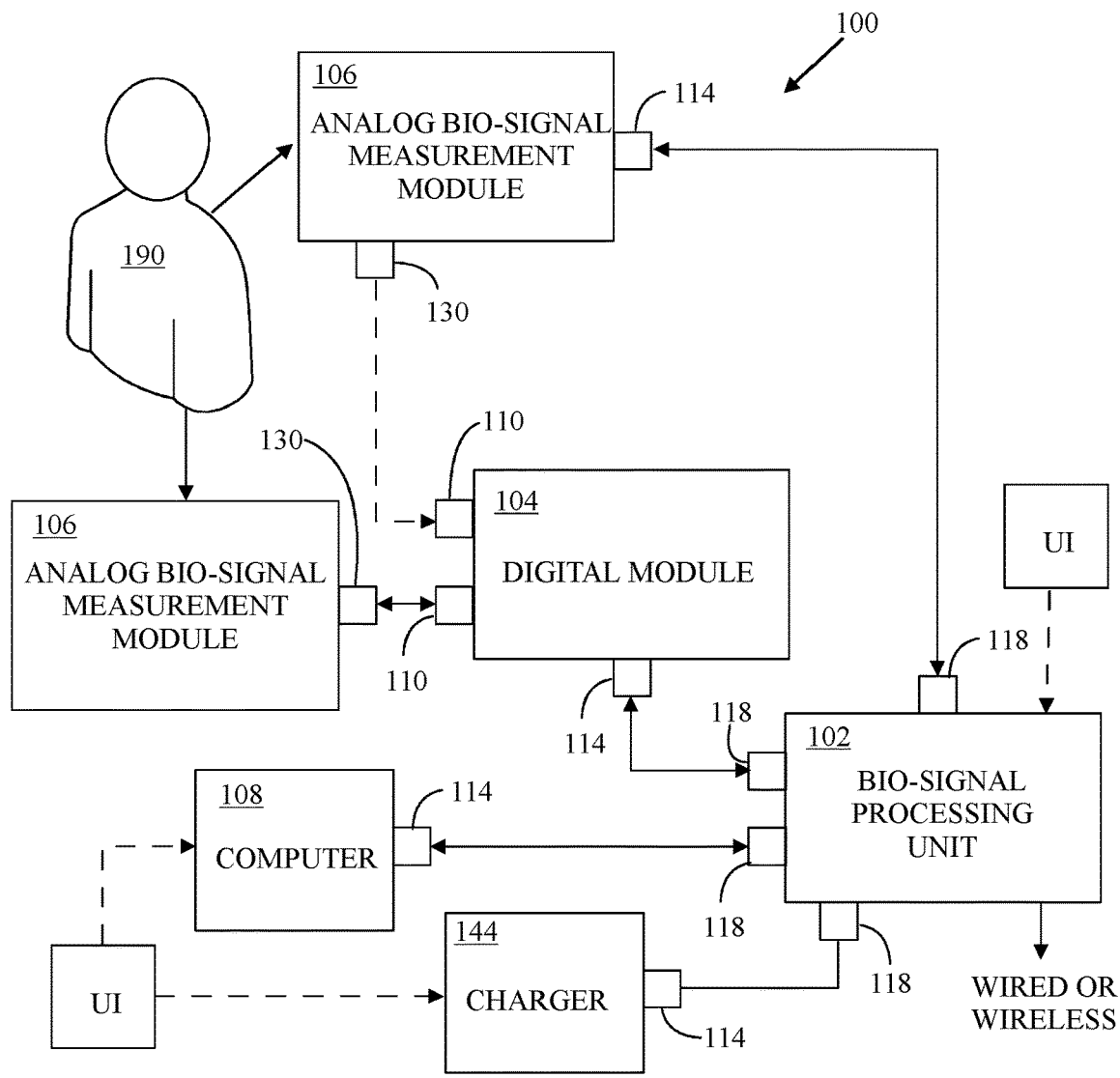

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

This document discusses an expansion of the possible uses of a standard 5-pin-USB-connector for bio-signal measurement devices (USB stands for Universal Serial Bus). The increase of the number of channels and the expansion of the possible measured signals has been provided in a simple manner for the USB, which is a standard compliant towards an external device such as a PC (Personal Computer).

A purpose of this document is to teach how to offer more channels and accessories to be connected to a bio-signal processing unit 102 via a robust and industry standard 5-pin-USB-connector interface such as the USB 2.0 interface while retaining the 5-pin-USB-connector interface i.e. the USB 2.0 compliant interface.

A user may need to perform three different things with the same device interface:

1. Communicate with a PC 108 for transferring data and recharging a device battery 142 of the bio-signal processing unit 102
2. Measure a single channel (3 pins) analog ECG data via Lead-set or Electrode Patch when using an internal AFE (Active Front End)
3. Connect at least one of the following extended external units:
   a. AFE unit to the device to obtain 3-, 5- or 12-lead ECG measurement (may require more than 10 pins to connect on analog level)
   b. SpO$_2$+ECG-unit
   c. Some other vital signal monitoring signal.

A working principle to obtain this functionality may be based on use of chained USB 2.0 multiplexers and lead-type detection to select the operation mode. In feature 2), the electrode potential may be fed directly to an A/D-converter of a bio-signal processing unit 102, because the AFE is a general name for a component that may include anti-aliasing filtering, multiplexing, potentially amplifying, potentially other filtering and A/D-converting. Note that five contact electrodes may carry bio-signal information in three channels.

FIG. 1 illustrates an example of a physiological measurement system 100 that may comprise the bio-signal processing unit 102, a digital module 104, an analog bio-signal measurement module 106, a computer 108 and a charger 144. The term bio-signal refers to an electrical signal that carries biological or physiological information in a time-varying manner.

The bio-signal processing unit 102 performs data processing. The bio-signal processing unit 102 may be an electronic device, which may convert an analog bio-signal it receives to a digital bio-signal. The bio-signal processing unit 102 may also receive digital bio-signals. The bio-signal processing unit 102 may also filter the bio-signal in an analog or in a digital form. Additionally or alternatively, the bio-signal processing unit 102 may perform data processing of the bio-signal, and it may also store data of the bio-signal and/or a result of its processing. The bio-signal may be related to heart rate variability, electrocardiogram, electromyogram, electroencephalogram or the like for example.

Figure 2:
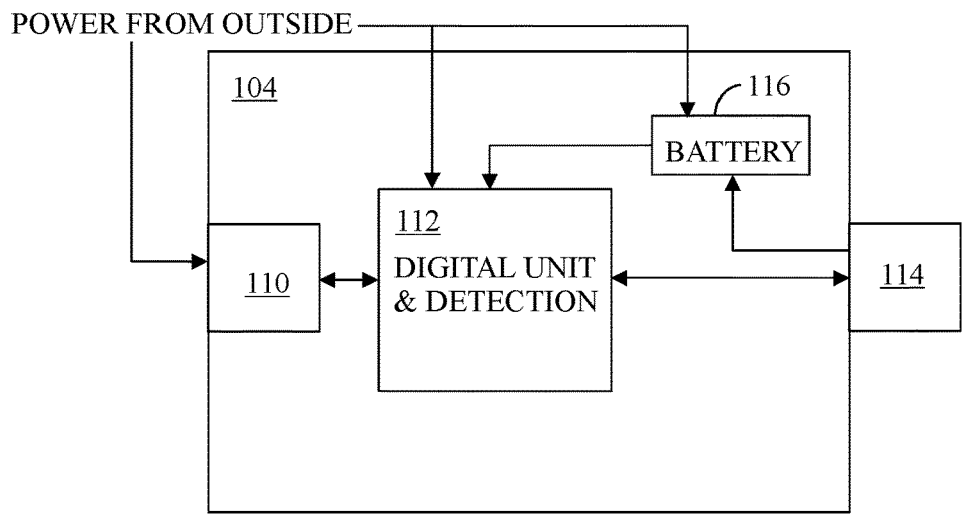
FIG. 2 illustrates an example of a digital module.

The digital module 104, an example of which is illustrated in greater detail in FIG. 2, comprises at least one connector 110, which configured to receive at least one analog bio-signal. The digital module 104 also comprises a digital unit 112, which comprises a first analog-to-digital converter, for example, and perhaps performs filtering and data processing. The digital unit 112 is configured to convert the at least one analog bio-signal into a digital signal form. The digital module 104 further comprises a first 5-pin-USB-connector 114, which is configured to output the at least one bio-signal in the digital signal form. Additionally, the digital module 104 may comprise a first battery 116. In an embodiment, the first USB-connector 114 may be a male USB-connector, for example. In an embodiment, the first USB-connector 114 may be a female USB-connector, for example. In an embodiment, the first USB-connector 114 may be a USB-A-connector. In an embodiment, the first USB-connector 114 may be a USB-C-connector. The digital module 104 allows connection with the at least one extended external units not otherwise possible when using 5-pin-USB-coupling. The digital module 104 may comprise also patient protection circuit which protects the person 190 against high voltages of a defibrillation device or the like, for example.

In an embodiment, the digital module 104 may receive the analog bio-signal directly from at least one analog sensor, such as the ECG-, EEG- or SpO$_2$-sensor, for example, measuring to the person 190. The at least one sensor may be a part of the digital module 104 and hence the digital module 104 may perform at least one bio-signal measurement by itself, or the digital module 104 may be connected with the sensor using a coupling between a USB-connector 114 and a counter-USB-connector 118, for example.

In an embodiment, the digital module 104 may receive the analog bio-signal from the analog bio-signal measurement module 106.

Figure 3:
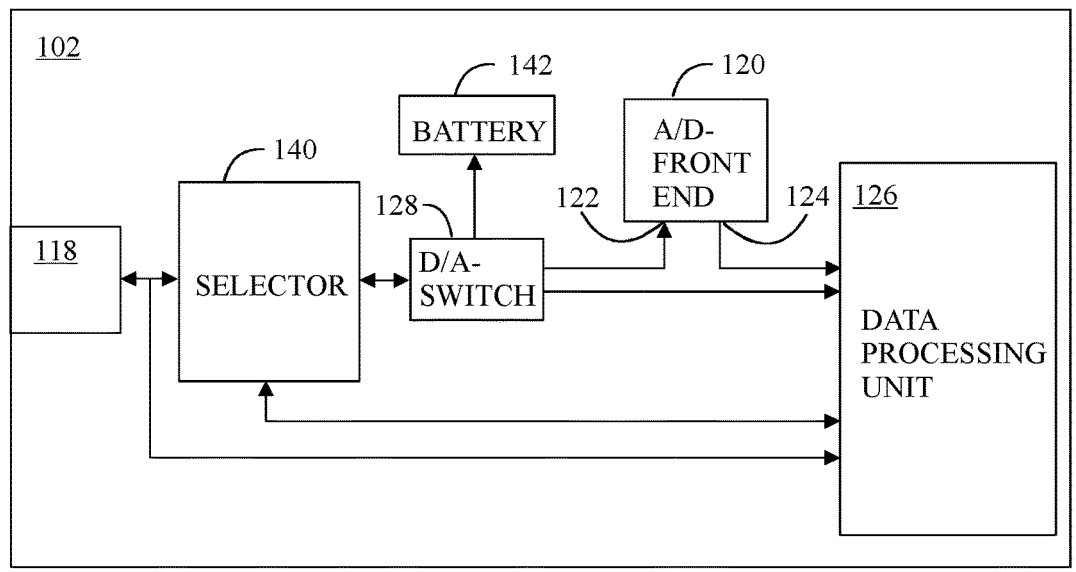
FIG. 3 illustrates an example of a bio-signal processing unit.

The bio-signal processing unit 102, an example of which is illustrated in greater detail in FIG. 3, comprises a counter 5-pin-USB-connector 118, which is configured to be connected with the first USB-connector 114 and receive the at least one bio-signal in the digital signal form from the digital module 104. Alternatively or additionally, the bio-signal processing unit 102 is configured to receive at least one bio-signal in an analog signal form from the first USB-connector 114, which is electrically coupled with the counter USB-connector 118. Although FIG. 1 shows a plurality of counter USB-connectors 118, in an embodiment the bio-signal processing unit 102 may have only one counter USB-connector 118, and an analog signal source and a digital signal source may alternatively be connected with the counter USB-connector 118. In an embodiment, the bio-signal processing unit 102 may have a plurality of counter USB-connectors.

In an embodiment, the counter USB-connector 118 may be a male USB-connector, for example. In an embodiment, the counter USB-connector 118 may be a female USB-connector, for example. In an embodiment, the counter USB-connector 118 may be a USB-A-connector. In an embodiment, the counter USB-connector 118 may be a USB-C-connector.

The bio-signal processing unit 102 is configured to distinguish between the digital and analog signal forms received through the counter USB-connector 118. The bio-signal processing unit 102 is configured to perform an electric connection of the counter USB-connector 118 with an input 122 of an analog-to-digital converter circuit 120, an output 124 of which is electrically connected with a digital data processing unit 126 of the bio-signal processing unit 102, in response to detection of the analog signal form received from the counter USB-connector 118. In an embodiment, the analog-to-digital converter circuit 120 may feed the bio-signal converted into the digital signal form to a digital communication bus of the digital data processing unit 126.

The bio-signal processing unit 102 is configured to perform an electric connection of the counter USB-connector 118 with the digital data processing unit 126 in response to detection of the digital signal form received from the counter USB connector 118. In an embodiment, the bio-signal processing unit 102 may feed the bio-signal that is in the digital signal form to the digital communication bus of the digital data processing unit 126.

In an embodiment, the bio-signal processing unit 102 comprises an analog-digital switch 128, which may distinguish between the analog and digital signal forms, and may perform the electric connection of the counter USB-connector 118 with the input 122 of the analog-to-digital converter circuit 120. The analog-digital switch 128 may also perform the electric connection of the counter USB-connector 118 with the digital data processing unit 126.

In an embodiment, the bio-signal processing unit 102 and the analog-digital switch 128 may distinguish the analog and digital signal forms that are to be received by feeding an electric impulse to the counter USB-connector 118 which is also received by the digital module 104 in the case it is connected with the bio-signal processing unit 102. Then the digital module 104 may utilize energy of the electric impulse and respond to the electric impulse with a predetermined signal, which is characteristic to the digital module 104. Then the bio-signal processing unit 102 may recognize the digital module 104 based on its response and is prepared for a reception in the digital signal form. An electric impulse may be understood to be an electric power variation that has duration equal to or shorter than an average variation of the bio-signal and that is fed and/or propagates in one direction, for example, without limiting to this.

In an embodiment, the digital module 104 may send a predetermined signal, which is characteristic to the digital module 104, to the bio-signal processing unit 102 based on energy not fully or at all coming from the electric impulse after and/or in response to the connection with the bio-signal processing unit 102. The energy for the predetermined signal and/or operation of the digital module 104 may come from the first battery 116 and/or from an outside electric energy source such as a national or transnational electric grid with power stations. The outside electric energy source may be isolated such that it is safe to use. The digital module 104 may send the predetermined signal in response to or independent from the electric impulse from the bio-signal processing unit 102.

In an embodiment, the physiological measurement system 100 comprises at least one of the following analog bio-signal measurement modules 106: a 3-lead electrocardiogram (ECG) monitoring sensor, a 5-lead electrocardiogram monitoring sensor, a 12-lead electrocardiogram monitoring sensor system, an oxygen sensor, a temperature sensor, a blood pressure sensor, a heart rate sensor and a respiratory sensor.

The ECG measurement, which a person skilled in the art is familiar with, per se, provides voltage of the electrical activity of the heart as a function of time detected with electrodes on the skin of a person 190. The number of the electrodes may be 3 (3-lead ECG), 5 (5-lead ECG) or 12 (12-lead ECG), for example. The ECG-sensor has output in the analog signal form.

The oxygen sensor, which a person skilled in the art is familiar with, per se, may be used to measure oxygen saturation ($SpO_2$) of the person 190 in an optical manner. It outputs its results in the analog signal form. It is simple, economic, safe and convenient.

Body temperature of the person 190 may also be measured electrically such that the output is in the analog signal form. The medical thermometer may be placed in the mouth, in the rectum, in the ear, under the armpit, or the temperature may be detected with or without contact with the skin of the person 190 or the mammal from the forehead, for example.

Blood pressure of the person 190 may be measured electrically such that the output is in the analog signal form. A person skilled in the art is familiar with the electrical blood pressure measurement, per se. In a similar manner, heart rate of the person 190 may be measured electrically such that the output is in the analog signal form. A person skilled in the art is familiar with the electrical heart rate measurement, per se.

Any of the at least one analog bio-signal measurement module 106 may output the at least one bio-signal in the analog form, and the digital module 104 receives the at least one analog bio-signal through at least one counter connector 130 of the at least one analog bio-signal measurement module 106 connected with the at least one connector 110 of the at least one digital module 104.

In an embodiment, the digital module 104 may comprise only one connector 110 and only one analog bio-signal measurement module 106 can be connected with it at a time. In this embodiment, a plurality of the analog bio-signal measurement modules 106 may be connected with the digital module 104 alternatively.

In an embodiment, the digital module 104 may comprise a number of connectors 110 and the same number of the analog bio-signal measurement modules 106 may be connected with it at a time.

In an embodiment, any or all of the one or more connectors 110 may be USB-connectors similar to the USB-connector 114. In an embodiment, connections may be alternative such that either there is a connection between the USB-connector 114 and the counter USB-connector 118, or there is a connection between the USB-connector 114 and the connector 110.

Figure 4:
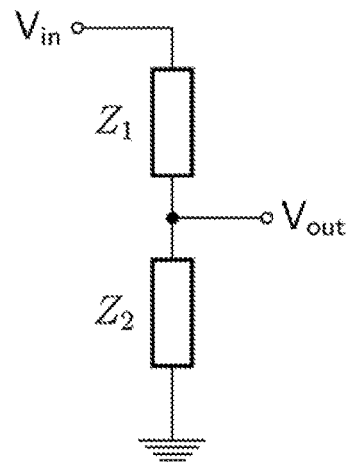
FIG. 4 illustrates an example how recognition/identification of a digital module, an analog bio-signal measurement module, a computer and a charger, for example, may be performed.

In an embodiment which is illustrated in FIG. 4, the bio-signal processing unit 102 may send an electric impulse to the counter USB-connector 118 in response to detection of lack of a standard operational voltage in the counter USB-connector 118. In an embodiment, the bio-signal processing unit 102 may send the electric impulse under control of the digital data processing unit 126. In an embodiment, the electric impulse may be an electric current pulse, for example.

In an example of FIG. 4, two impedances/resistors $Z_1$ and $Z_2$ form an electric coupling. In general, the electric coupling may be more complicated and it may have more electric components. The voltage $V_{in}$ denotes the electric impulse, $Z_1$ may denote an internal impedance/resistance of the bio-signal processing unit 102, $Z_2$ may denote an identification impedance/resistance of an electric device connected with the counter USB-connector 118 and $V_{out}$ denotes a point at which the identification may be performed.

In a situation where no device has been connected with the counter-USB-connector 118 causes the impedance/resistance $Z_2$ to be very high corresponding to infinity, which can be recognized by the bio-signal processing unit 102/the digital data processing unit 126. In a situation where the impedance/resistance $Z_2$ is a function of the device connected with the counter-USB-connector 118 may allow the bio-signal processing unit 102/the digital data processing unit 126 to recognize and identify the device. In this case, the voltage $V_{out}=V_{in}*Z_2/(Z_1+Z_2)$, which depends on $Z_2$, which reveals the device. The device may be the digital module 104, the analog bio-signal measurement module 106, the computer 108 and/or the charger 144, for example.

Alternatively, $Z_1$ may denote identification impedance/resistance of an electric device connected with the counter USB-connector 118 and $Z_2$ may denote internal impedance/resistance of the bio-signal processing unit 102. In a situation where the impedance/resistance $Z_1$ is a function of the device connected with the counter-USB-connector 118 may allow the bio-signal processing unit 102/the digital data processing unit 126 to recognize and identify the device. Also in this case, the voltage $V_{out}=Vin*Z_2/(Z_1+Z_2)$, which depends on $Z_1$, which reveals the device.

In an embodiment, the electric impulse may be sent only when instructed by a user through a user interface UI, which may be a part of the bio-signal processing unit 102, connected directly with the bio-signal processing unit 102 in a wired or wireless manner or connected through the computer 108 or the charger 144. In an embodiment, the electric impulse may be sent in response to the connection between the counter-USB-connector 118 and the USB-connector 114. Namely, the digital data processing unit 126 may have a logic functionality that recognizes an operational voltage at the USB-connector 114, the operational voltage being about 3.75V to about 5.5V, for example. If the operational voltage is not detected, the bio-signal processing unit 102 may send, under control of the digital data processing unit 126 the electric impulse, which may about 2V, for example. The electric impulse ($V_{in}$) may be sent to the first pin of the USB-connector, for example.

In an embodiment, the digital module 104, the first USB-connector 114 which is in connection with the counter USB-connector 118, may send a predetermined electric signal back to the bio-signal processing unit 102 in response to the electric impulse.

The digital data processing unit 126 of the bio-signal processing unit 102 may acknowledge the digital module 104 based on the predetermined electric signal that it receives.

In an embodiment, the physiological measurement system 100 may comprise at least one analog bio-signal measurement module 106, which may measure at least one bio-signal of a mammal such as a person 190. The at least one analog bio-signal measurement module 106 may comprise a counter connector 130, which may be connected with the connector 110 of the digital module 104 for providing the digital module 104 with a bio-signal of the analog form.

In an embodiment, the physiological measurement system 100 may comprise at least one analog bio-signal measurement module 106, which may measure at least one bio-signal of a mammal such as a person 190. The at least one analog bio-signal measurement module 106 may comprise a second USB-connector 114, which may output the at least one analog bio-signal, the second USB-connector 114 and the first USB connector 118 being configured to connect with each other.

That is, it is possible that at least one of the at least one analog bio-signal measurement module 106 can be directly connected with the bio-signal processing unit 102. Alternatively or additionally, it is possible that at least one of the at least one analog bio-signal measurement module 106 can be connected with the digital module 106 which can be connected with the bio-signal processing unit 102.

In an embodiment, the bio-signal processing unit 102 may send an electric current impulse to the counter USB-connector 110 in response to lack of a standard operational voltage in the counter USB-connector 110. The sending may be performed under control of the digital data processing unit 126. The bio-signal processing unit 102 and typically the digital data processing unit 126 may detect a type of an analog bio-signal measurement module of the at least one analog bio-signal measurement module 106 that is in an electric connection with the counter USB-connector 110.

In an embodiment, the physiological measurement system 100 may comprise a computer 108, which comprises a third USB connector 114 or is configured to connect using the third USB-connector 114 with the bio-signal processing unit 102.

The bio-signal processing unit 102 may detect, and often it is the data processing unit 126 that may detect, the computer 108 based on a standard operational voltage of the third USB-connector 114 coming from the computer 108 in response to electrical connection between the counter USB-connector 118 and the third USB-connector 114. The bio-signal processing unit 102 may electrically connect the digital data processing unit 126 with the counter USB-connector 118 often under control of the digital data processing unit 126 for preparation of a data transfer between the bio-signal processing unit 102 and the computer 108. In an embodiment, the computer 108 may command the bio-signal processing unit 102 to send full or partial contents of data the bio-signal processing unit 102 has in its memory. In one or more embodiments, the computer 108 may send data to the bio-signal processing unit to be saved there.

In an embodiment an example of which is illustrated in FIG. 3, the bio-signal processing unit 102 may comprise a selector 140, which may comprise a multiplexer, for example. The selector 140 may detect, prior to the distinction between the analog and digital signal forms, the computer 108 based on the standard operational voltage of the third USB-connector 114. Then the selector 140 may electrically connect the digital data processing unit 126 with the counter USB-connector 118, which allows data transfer between the computer 108 and the bio-signal processing unit 102 through the USB-connection.

In an embodiment an example of which is illustrated in FIG. 3, the bio-signal processing unit 102 may electrically connect the battery 142 of the bio-signal processing unit 102 with the counter USB-connector 118 for charging the battery 142 of the bio-signal processing unit 102 in response to detection of the computer 108, which may provide the standard operational voltage.

In an embodiment, the selector 140 of the bio-signal processing unit 102 may detect the charger 144 based on the standard operational voltage of the third USB-connector 114. The bio-signal processing unit 102 may electrically connect the battery 142 of the bio-signal processing unit 102 with the counter USB-connector 118 for charging the battery 142 of the bio-signal processing unit 102. The charger 144 may be separate charger 144 like that illustrated in FIG. 1 or the charger 144 may locate inside the computer 108, for example. The separate charger 144 may comprise a fourth USB-connector 114 for connecting the charger 144 with the counter USB-connector 118 of the bio-signal processing unit 102.

Figure 5:
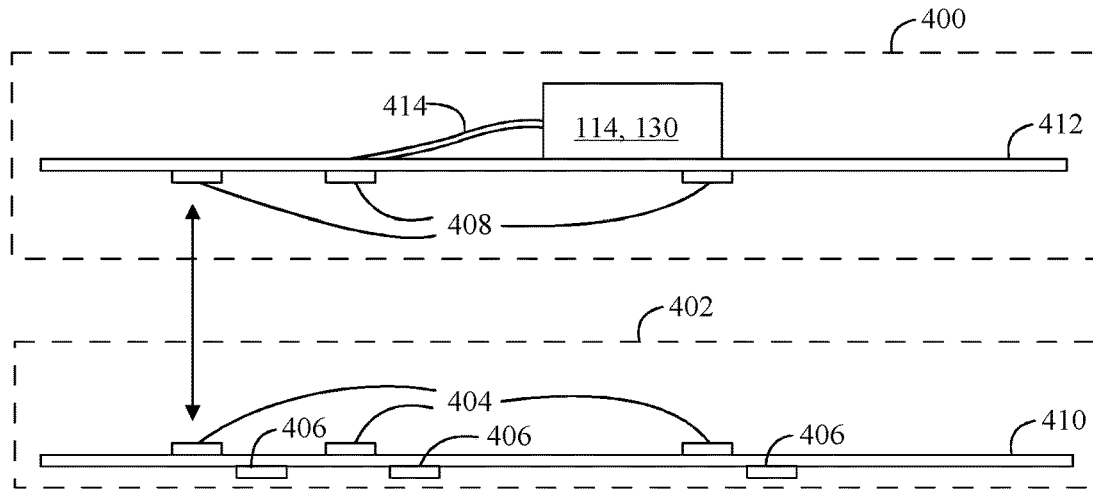
FIG. 5 illustrates an example of an analog bio-signal measurement module.

FIG. 5 illustrates an example of the analog bio-signal measurement module 106 which is configured to measure the ECG, for example. The bio-signal measurement module 106 may comprise an electrode support structure 402 and a connection structure 400. The electrode support structure 402 may comprise a number of tool-less electric connection elements 404 and electrodes 406. A number of tool-less electric connection elements 404 corresponds to the number of tool-less counter connection elements 408 of the connection structure 400. In that manner, the electrode support structure 402 may be disposable and as simple as possible, and the connection structure may be used a plurality of times.

The electrode support structure 402 may have a PET-layer 410 with AgCl-printed electrodes 406, for example. The connection structure 400 may comprise circuit board 412, such as a rigid-flex PCB, and the USB-connector 114 may be on the circuit board 412.

A wire connection 414 may connect the tool-less counter electric connection elements 408 and the USB-connector 114 and/or the connector 130.

Figure 6:
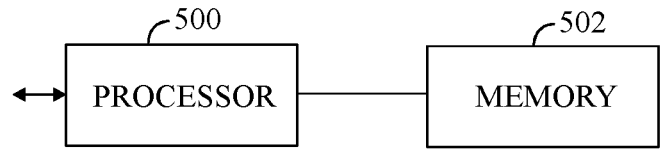
FIG. 6 illustrates an example of a data processing unit of the analog bio-signal measurement module.

In an embodiment an example of which is shown in FIG. 6, the data processing unit 126 may comprise one or more processors 500, and one or more memories 502 that may include a computer program code. The one or more memories 502 and the computer program code may, with the one or more processors 500, cause the data processing unit 126 at least to process the bio-signal received from the person 190 or from an animal.

Also one aspect to consider and use in a manner described in this document is that USB 2.0 micro-USB-connector male connectors for disposable accessories are relatively easy to find at reasonable prices. The same applies also to the corresponding counter USB-connectors, i.e. female USB 2.0 micro-USB-connectors.

Figure 7:
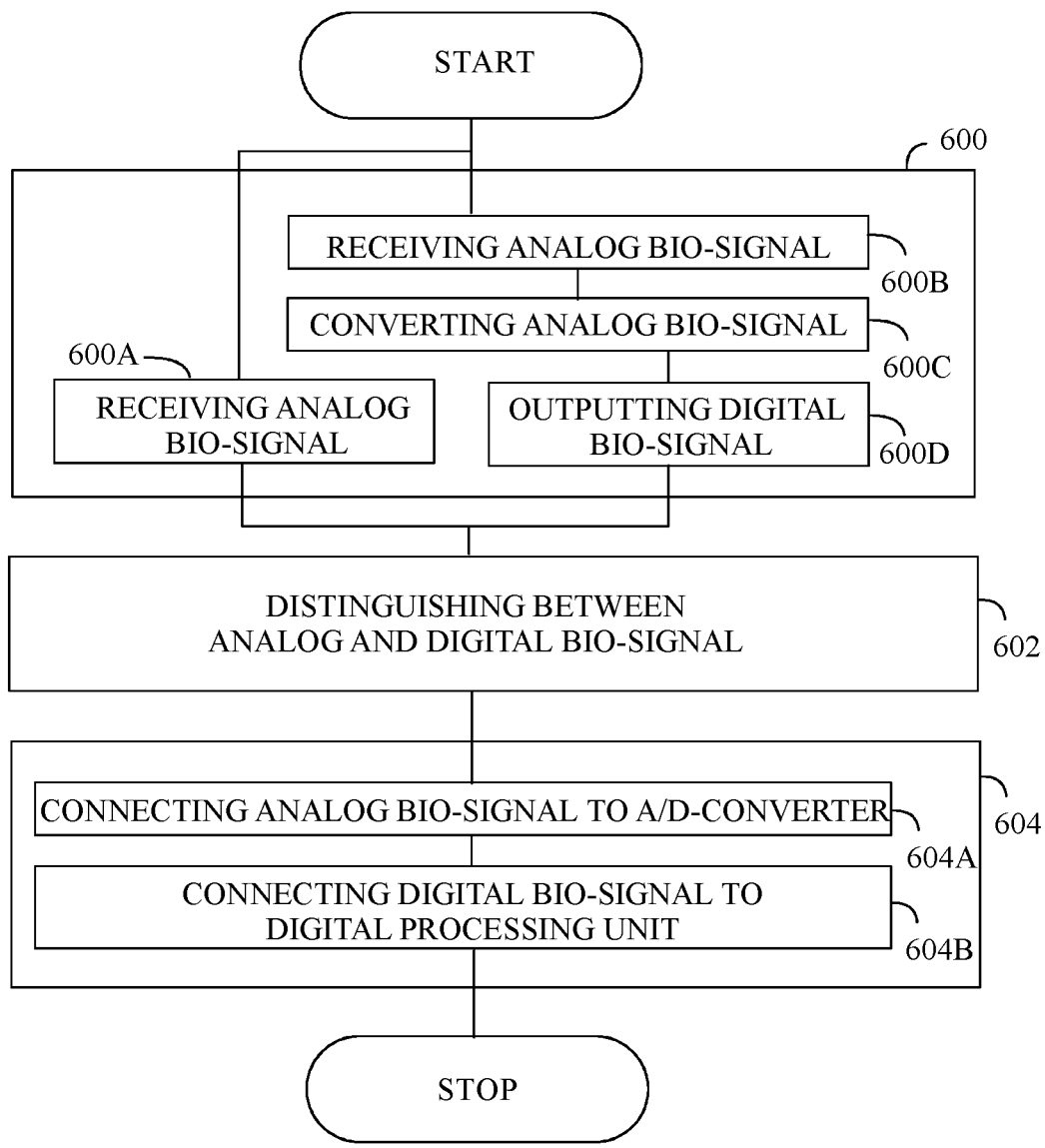
FIG. 7 illustrates of an example of a flow chart of a measuring method.

FIG. 7 is a flow chart of the measurement method. In step 600, at least one bio-signal in a digital form is received, or alternatively at least one bio-signal in an analog form is received 600A, through a counter USB-connector 118 of a bio-signal processing unit 102, the at least one bio-signal in the digital form coming from a digital module 104, which
  receives 600B at least one bio-signal in the analog form,
  converts 600C the at least one signal of the analog form by the digital unit 112 of the digital module 104 into the digital form, and
  outputs 600D said at least one bio-signal in the digital form through a first USB connector 114, which is connected with the counter USB-connector 118, to the bio-signal processing unit 102;
  distinguishing 602, by the bio-signal processing unit 102, between the analog and digital signal forms; and
  performing 604 the following:
  connecting 604A electrically the counter USB-connector 118 with an input 122 of an analog-to-digital converter circuit 120 of the bio-signal processing unit 102, an output 124 of the second analog-to-digital converter 120 being electrically connected with a digital data processing unit 126 of the bio-signal processing unit 102, in response to detection of the analog signal form received from the counter USB-connector 118, and
  connecting 604B electrically the counter USB-connector 118 with the digital data processing unit 126 in response to detection of the digital signal form received from the counter USB connector 118.

The method shown in FIG. 7 may be implemented as a logic circuit solution or computer program. The computer program may be placed on a computer program distribution means for the distribution thereof. The computer program distribution means is readable by a data processing device, and it encodes the computer program commands, carries out the measurements and optionally controls the processes on the basis of the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

What is taught above may allow to use USB 2.0 series connectors in the future with expanding signal offering. This may result in one or more advantages such as:

Robust industry proven connector family and proven concept

Small form factor

Cheap connectors, cheap to implement and overall inexpensive solution

Widely accepted interface for PC's etc.

Over-mouldable connectors

No requirements for expensive IC-circuitry on communication cables

No proprietary connectors

Possibility to use old accessories while allowing adaptation to future signalling In general, what is taught in this document enables the expansion of the use of small pin-count connectors in untraditional way.

It will be obvious to a person skilled in the art that, as technology advances, the inventive concept can be implemented in various ways. The invention and its embodiments are not limited to the example embodiments described above but may vary within the scope of the claims.

The invention claimed is:

1. A bio-signal processing unit, comprising:
a counter 5-pin-USB-connector, which is configured to be connected with a first 5-pin-USB-connector of a digital module providing at least one bio-signal in a digital form, and receive the at least one bio-signal in the digital signal form, and alternatively receive at least one bio-signal in an analog signal form; and
wherein the bio-signal processing unit is configured to distinguish between the digital and analog signal forms received through the counter 5-pin-USB-connector and perform:
an electric connection of the counter 5-pin-USB-connector with an input of an analog-to-digital converter circuit, an output of which is electrically connected with a digital data processing unit of the bio-signal processing unit, in response to detection of the analog signal form received from the counter 5-pin-USB-connector, and
an electric connection of the counter 5-pin-USB-connector with the digital data processing unit in response to detection of the digital signal form received from the counter 5-pin-USB connector;
the bio-signal processing unit further comprising a selector electrically connected to the counter 5-pin-USB connector, the selector being configured to detect voltage existing on the counter 5-pin-USB connector; and
wherein the bio-signal processing unit is further configured to recognize and identify different device categories connected in the counter 5-pin-USB connector based on the voltage on the counter 5-pin-USB connector.

2. A physiological measurement system, wherein the physiological measurement system comprises:
a digital module, which is configured to receive at least one analog bio-signal, a digital unit configured to convert the at least one analog bio-signal into a digital signal form, and a first 5-pin-USB-connector configured to output the at least one bio-signal in the digital signal form;
a bio-signal processing unit, which comprises a counter 5-pin-USB-connector, which is configured to be connected with the first 5-pin-USB-connector and receive the at least one bio-signal in the digital signal form from the digital module, and alternatively receive at least one bio-signal in an analog signal form therethrough; and
the bio-signal processing unit is configured to distinguish between the digital and analog signal forms received through the counter 5-pin-USB-connector and perform:
an electric connection of the counter 5-pin-USB-connector with an input of an analog-to-digital converter circuit, an output of which is electrically connected with a digital data processing unit of the bio-signal processing unit, in response to detection of the analog signal form received from the counter 5-pin-USB-connector, and
an electric connection of the counter 5-pin-USB-connector with the digital data processing unit in response to detection of the digital signal form received from the counter 5-pin-USB connector;
wherein the bio-signal processing unit further comprising a selector electrically connected to the counter 5-pin-USB connector, the selector being configured to detect voltage existing on the counter 5-pin-USB connector; and
wherein the bio-signal processing unit is further configured to recognize and identify different device categories connected in the counter 5-pin-USB connector based on the voltage on the counter 5-pin-USB connector.

3. The physiological measurement system of claim 2, wherein the bio-signal processing unit comprises an analog/digital switch configured to distinguish between the analog and digital signal forms, and perform the electric connection of the counter 5-pin-USB-connector with the input of an analog-to-digital converter circuit, and the electric connection of the counter 5-pin-USB-connector with the digital data processing unit.

4. The physiological measurement system of claim 2, wherein the physiological measurement system comprises at least one of the following analog bio-signal measurement modules:
a 3-lead electrocardiogram monitoring sensor, a 5-lead electrocardiogram monitoring sensor, a 12-lead electrocardiogram monitoring sensor system, an oxygen sensor, a temperature sensor, a blood pressure sensor, a heart rate sensor and a respiratory sensor,
which are configured to output the at least one analog bio-signal for the digital module to receive the at least one analog signal through at least one counter connector of the sensors connected with at least one connector of the digital module.

5. The physiological measurement system of claim 2, wherein the bio-signal processing unit is configured to send an electric impulse to the counter 5-pin-USB-connector in response to detection of lack of a standard operational voltage in the counter 5-pin-USB-connector,
the digital module, the first 5-pin-USB-connector of which is in connection with the counter 5-pin-USB-connector, is configured to send a predetermined electric signal back to the bio-signal processing unit in response to the electric impulse, and
the bio-signal processing unit is configured to acknowledge the digital module based on the predetermined electric signal.

6. The physiological measurement system of claim 2, wherein the physiological measurement system comprises at least one analog bio-signal measurement module, which is configured to measure at least one bio-signal of a mammal and comprises a counter connector which is configured to be connected with a connector of the digital module for providing the digital module with a bio-signal of the analog form.

7. The physiological measurement system of claim 2, wherein the physiological measurement system comprises at least one analog bio-signal measurement module, which is configured to measure at least one bio-signal of a mammal and comprises a second 5-pin-USB-connector, which is configured to output the at least one analog bio-signal, the second 5-pin-USB-connector and the first 5-pin-USB connector being configured to connect with each other.

8. The physiological measurement system of claim 7, wherein the bio-signal processing unit is configured to send an electric current impulse to the counter 5-pin-USB-connector in response to lack of a standard operational voltage, and detect a type of an analog bio-signal measurement module of the at least one analog bio-signal measurement module that is in an electric connection with the counter 5-pin-USB-connector.

9. The physiological measurement system of claim 2, wherein the physiological measurement system comprises a computer, which comprises a third 5-pin-USB connector or is configured to connect with the third 5-pin-USB-connector; and
the bio-signal processing unit is configured to detect the computer based on a standard operational voltage of the third 5-pin-USB-connector in response to electrical connection between the counter 5-pin-USB-connector and the third 5-pin-USB-connector, and electrically connect the digital data processing unit with the counter 5-pin-USB-connector for a data transfer between the bio-signal processing unit and the computer.

10. The physiological measurement system of claim 9, wherein
the selector is configured to detect, prior to the distinction between the analog and digital signal forms, the computer based on the standard operational voltage of the third 5-pin-USB-connector, and electrically connect the digital data processing unit with the counter 5-pin-USB-connector.

11. The physiological measurement system of claim 10, wherein the bio-signal processing unit is configured to electrically connect a battery of the bio-signal processing unit with the counter 5-pin-USB-connector for charging the battery of the bio-signal processing unit in response to detection of the computer, which is configured to provide the standard operational voltage.

12. The physiological measurement system of claim 10, wherein the selector of the bio-signal processing unit is configured to detect a charger based on the standard operational voltage of the third 5-pin-USB-connector, and electrically connect the battery of the bio-signal processing unit with the counter 5-pin-USB-connector for charging the battery of the bio-signal processing unit.

13. The physiological measurement system of claim 2, wherein the bio-signal processing unit comprises
one or more processors; and
one or more memories including computer program code;
the one or more memories and the computer program code configured to, with the one or more processors, cause the bio-signal processing unit at least to:
distinguish between the digital and analog signal forms received through the counter 5-pin-USB-connector and perform:
the electric connection of the counter 5-pin-USB-connector with the input of the analog-to-digital converter circuit, the output of which is electrically connected with the digital data processing unit of the bio-signal processing unit, in response to the detection of the analog signal form received from the counter 5-pin-USB-connector, and
the electric connection of the counter 5-pin-USB-connector with the digital data processing unit in response to the detection of the digital signal form received from the counter 5-pin-USB connector.

14. A physiological measurement method, the method comprising:
receiving, through a counter 5-pin-USB-connector of a bio-signal processing unit, at least one bio-signal in a digital form, or alternatively at least one bio-signal in an analog form, the at least one bio-signal in the digital form coming from a digital module, which
receives at least one bio-signal in the analog form,
converts the at least one signal of the analog form by a digital unit of the digital module into the digital form, and
outputs said at least one bio-signal in the digital form through a first 5-pin-USB connector, which is connected with the counter 5-pin-USB-connector, to the bio-signal processing unit;
distinguishing, by the bio-signal processing unit, between the analog and digital signal forms;
wherein the counter 5-pin-USB-connector is connected electrically with an input of an analog-to-digital converter circuit of the bio-signal processing unit, an output of the analog-to-digital converter circuit being electrically connected with a digital data processing unit of the bio-signal processing unit, in response to detection of the analog signal form received from the counter 5-pin-USB-connector, and
wherein the counter 5-pin-USB-connector is connected electrically with the digital data processing unit in response to detection of the digital signal form received from the counter 5-pin-USB connector; and
detecting voltage existing on the counter 5-pin-USB connector via a selector electrically connected to the counter 5-pin-USB connector, the bio-signal processing unit comprising the selector; and
wherein the bio-signal processing unit is further configured to recognize and identify different device categories connected in the counter 5-pin-USB connector based on the voltage on the counter 5-pin-USB connector.

15. The method of claim 14, further comprising measuring at least one bio-signal of a mammal via at least one analog bio-signal measurement module comprising a second 5-pin-USB-connector that is configured to output the at least one analog bio-signal, the second 5-pin-USB-connector and the first 5-pin-USB connector being configured to connect with each other.

16. The method of claim 15, wherein the bio-signal processing unit is configured to send an electric current impulse to the counter 5-pin-USB-connector in response to lack of a standard operational voltage, and detect a type of an analog bio-signal measurement module of the at least one analog bio-signal measurement module that is in an electric connection with the counter 5-pin-USB-connector.

17. The method of claim 14, wherein the physiological measurement system comprises a computer, which comprises a third 5-pin-USB connector or is configured to connect with the third 5-pin-USB-connector; and wherein the bio-signal processing unit is configured to detect the computer based on a standard operational voltage of the third 5-pin-USB-connector in response to electrical connection between the counter 5-pin-USB-connector and the third 5-pin-USB-connector, and electrically connect the digital data processing unit with the counter 5-pin-USB-connector for a data transfer between the bio-signal processing unit and the computer.

18. The method of claim 17, wherein the selector is configured to detect, prior to the distinction between the analog and digital signal forms, the computer based on the standard operational voltage of the third 5-pin-USB-connector, and electrically connect the digital data processing unit with the counter 5-pin-USB-connector.

19. The method of claim 18, wherein the bio-signal processing unit is configured to electrically connect a battery of the bio-signal processing unit with the counter 5-pin-USB-connector for charging the battery of the bio-signal processing unit in response to detection of the computer, which is configured to provide the standard operational voltage.

20. The method of claim 18, wherein the selector of the bio-signal processing unit is configured to detect a charger based on the standard operational voltage of the third 5-pin-USB-connector, and electrically connect the battery of the bio-signal processing unit with the counter 5-pin-USB-connector for charging the battery of the bio-signal processing unit.

* * * * *